(12) United States Patent
Pinsky et al.

(10) Patent No.: US 11,065,064 B2
(45) Date of Patent: Jul. 20, 2021

(54) CALIBRATION OF A RIGID ENT TOOL

(71) Applicant: Biosense Webster (Israel) Ltd., Yokneam (IL)

(72) Inventors: Yoav Pinsky, Bet Keshet (IL); Akram Zoabi, Kfar Masser (IL); Itamar Bustan, Zichron Ya'acov (IL); Michal Alroy Levy, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 696 days.

(21) Appl. No.: 15/812,059

(22) Filed: Nov. 14, 2017

(65) Prior Publication Data

US 2019/0142521 A1     May 16, 2019

(51) Int. Cl.
*A61B 34/20* (2016.01)
*A61B 5/06* (2006.01)
(Continued)

(52) U.S. Cl.
CPC .............. *A61B 34/20* (2016.02); *A61B 5/062* (2013.01); *A61B 17/00234* (2013.01);
(Continued)

(58) Field of Classification Search
CPC ......... A61B 90/00; A61B 90/06; A61B 90/08; A61B 90/37; A61B 90/39; A61B 2090/3954; A61B 2090/397; A61B 2090/3958; A61B 2090/3983; A61B 34/20; A61B 2034/2051; A61B 2034/2072; A61B 2017/00725; A61B 5/061; A61B 5/062; A61B 2560/0223; A61B 17/24;
(Continued)

(56) References Cited

U.S. PATENT DOCUMENTS

| | | |
|---|---|---|
| 5,391,199 A | 2/1995 | Ben-Haim |
| 5,443,489 A | 8/1995 | Ben-Haim |
| | (Continued) | |

FOREIGN PATENT DOCUMENTS

WO    WO 1996/041119 A1    12/1996

OTHER PUBLICATIONS

Extended European Search Report and Written Opinion dated Apr. 16, 2019 for Application No. 18205875.0, 4 pages.

*Primary Examiner* — Carolyn A Pehlke
(74) *Attorney, Agent, or Firm* — Frost Brown Todd LLC (57) ABSTRACT

An apparatus, including a magnetic field generator, a first magnetic field sensor configured for attachment to a proximal end of a surgical tool configured for insertion into a body, and a calibration device that includes a second magnetic field sensor and a proximity sensor, wherein the field sensors generate respective location signals responsive to a magnetic field emanating from the generator and traversing the field sensors. The apparatus includes a control unit, which receives the signals from all the sensors, extracts respective location and orientation coordinates of the field sensors based on the signals, computes a conversion relation between the coordinates of the first sensor and a distal end of the tool that is brought into contact with the calibration device, and subsequently applies the conversion relation, together with the coordinates of the first sensor, in providing a visual indication of a location of the distal end inside the body.

20 Claims, 5 Drawing Sheets

(51) Int. Cl.
*A61B 17/00* (2006.01)
*A61B 17/24* (2006.01)
*A61B 1/233* (2006.01)
*A61B 90/00* (2016.01)
*A61B 5/00* (2006.01)
*A61B 5/0538* (2021.01)

(52) U.S. Cl.
CPC .............. *A61B 17/24* (2013.01); *A61B 1/233* (2013.01); *A61B 5/0084* (2013.01); *A61B 5/0538* (2013.01); *A61B 2017/00115* (2013.01); *A61B 2017/00199* (2013.01); *A61B 2017/00296* (2013.01); *A61B 2034/2051* (2016.02); *A61B 2034/2055* (2016.02); *A61B 2090/065* (2016.02); *A61B 2090/0811* (2016.02); *A61B 2560/0223* (2013.01)

(58) Field of Classification Search
CPC ........... A61B 2018/00982; A61B 2018/00988; A61B 10/04
See application file for complete search history.

(56) References Cited

U.S. PATENT DOCUMENTS

| | | | |
|---|---|---|---|
| 5,558,091 A | 9/1996 | Acker et al. | |
| 5,987,960 A * | 11/1999 | Messner | A61B 17/00 73/1.79 |
| 6,172,499 B1 | 1/2001 | Ashe | |
| 6,177,792 B1 | 1/2001 | Govari et al. | |
| 6,690,963 B2 | 2/2004 | Ben-Haim et al. | |
| 6,788,967 B2 | 9/2004 | Ben-Haim et al. | |
| 7,720,521 B2 | 5/2010 | Chang et al. | |
| 7,751,865 B2 * | 7/2010 | Jascob | A61B 5/062 600/424 |
| 7,831,082 B2 * | 11/2010 | Holsing | A61B 90/36 382/131 |
| 7,837,616 B2 * | 11/2010 | Tsuji | A61B 34/20 600/117 |
| 7,876,942 B2 | 1/2011 | Gilboa | |
| 8,190,389 B2 | 5/2012 | Kim et al. | |
| 10,070,971 B2 * | 9/2018 | Palmatier | A61F 2/4611 |
| 2003/0209096 A1 * | 11/2003 | Pandey | A61B 34/20 73/865.9 |
| 2004/0153191 A1 * | 8/2004 | Grimm | A61B 34/20 700/114 |
| 2006/0004286 A1 | 1/2006 | Chang et al. | |
| 2006/0063973 A1 * | 3/2006 | Makower | A61M 29/02 600/114 |
| 2006/0241397 A1 * | 10/2006 | Govari | A61B 5/062 600/424 |
| 2007/0265526 A1 * | 11/2007 | Govari | A61B 5/062 600/424 |
| 2010/0290690 A1 * | 11/2010 | Hartmann | A61B 6/4405 382/132 |
| 2011/0082467 A1 * | 4/2011 | Tien | A61B 90/06 606/130 |
| 2013/0006102 A1 | 1/2013 | Wilkes et al. | |
| 2017/0172458 A1 * | 6/2017 | Kato | A61B 5/067 |
| 2017/0238996 A1 * | 8/2017 | Frame | A61B 34/20 |
| 2018/0177390 A1 * | 6/2018 | Iannitti | A61B 1/00045 |
| 2018/0311051 A1 * | 11/2018 | Donaldson | A61F 2/4611 |
| 2020/0237446 A1 * | 7/2020 | Drain | A61B 17/16 |

* cited by examiner

CALIBRATION OF A RIGID ENT TOOL

FIELD OF THE INVENTION

The present invention relates generally to medical imaging, and specifically to calibrating a magnetic field sensor attached to a rigid surgical tool.

BACKGROUND OF THE INVENTION

A wide range of medical procedures involve placing objects, such as sensors, tubes, catheters, dispensing devices, and implants, within the body. Real-time imaging methods are often used to assist doctors in visualizing the object and its surroundings during these procedures. In most situations, however, real-time three-dimensional imaging is not possible or desirable. Instead, systems for obtaining real-time spatial coordinates of the internal object are often utilized.

U.S. Pat. No. 8,190,389 to Kim et al., describes devices and methods for tracking a location of a medical device within a body of a human or animal subject. The medical device includes a calibration rigid body having a receiving groove, a first calibration tip and a second calibration tip. To track the medical device, the first calibration tip can be positioned in a known position relative to an electromagnetic transmitter while obtaining at least one reading using the image guided surgery system, the second calibration tip can be positioned in a known position in relation to the electromagnetic transmitter while obtaining at least one additional reading using the image guided surgery system, and the image guided surgery system can be calibrated to the substantially fixed shape of the medical device based on the obtained readings.

U.S. Pat. No. 7,720,521 to Chang et al., describes devices, systems and methods for performing image guided interventional and surgical procedures. The system includes a working device that can be inserted into a subject's body and comprises a single sensor that receives signals from at least three transmitters. A computer can then analyze the received signals to compute (e.g., using triangulation) a three dimensional position of the sensor within the body.

U.S. Pat. No. 7,876,942 to Gilboa et al., describes a system and method for optical position measurement and guidance of a rigid or semi-flexible tool to a target. The system includes a camera attached to the tool, and a processing system that processes images from the camera to determine a location of the tool. In some embodiments, the system can help an operator guide the tool to the target by optically identifying fiducial reference points defined on the external surface of the body, deriving a plane containing the target, and presenting, to the operator, the tool tip and the target position on the plane.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The description above is presented as a general overview of related art in this field and should not be construed as an admission that any of the information it contains constitutes prior art against the present patent application.

SUMMARY OF THE INVENTION

There is provided, in accordance with an embodiment of the present invention, an apparatus, including a magnetic field generator, a first magnetic field sensor, a calibration device, and a control unit. The first magnetic field sensor is configured for attachment to a proximal end of a rigid surgical tool configured to be inserted into a living body, and the calibration device includes a second magnetic field sensor and a proximity sensor, wherein the first and the second field sensors generate respective location signals responsive to a magnetic field emanating from the magnetic field generator and traversing the sensors. The proximity sensor generates a proximity signal indicating a contact with the calibration device. The control unit receives the signals from all the sensors, extracts respective location and orientation coordinates of the magnetic field sensors based on the signals, computes a conversion relation between the coordinates of the first magnetic field sensor and a distal end of the tool that is brought into contact with the calibration device, and subsequently applies the conversion relation, together with the coordinates of the first magnetic field sensor, in providing a visual indication of a location of the distal end of the tool inside the body.

In some embodiments, the rigid surgical tool includes a rigid endoscope. In additional embodiments, the proximity sensor includes a contact indicator. In further embodiments, the proximity sensor can be selected from a group consisting of a force sensor, an optical sensor and an electrical sensor.

In one embodiment, the first magnetic field sensor is configured to be removably attached to the proximal end of the rigid surgical tool. In another embodiment, the calibration device is configured to be placed on a reference object. In supplemental embodiments, the reference object includes a surface of the living body.

In some embodiments, the apparatus includes a display configured to present the visual indication of the location of the distal end of the tool inside the body. In additional embodiments, the apparatus includes a memory, wherein the processor is configured to store the computed conversion relation to the memory, and to retrieve the conversion relation from the memory. In further embodiments, the conversion relation includes an orientation and a distance between the location of the first magnetic field sensor and a location of the distal end.

There is also provided, in accordance with an embodiment of the present invention, a method, including receiving, from a first magnetic field sensor attached to a proximal end of a rigid surgical tool, first location signals responsive to a magnetic field emanating from a magnetic field generator and traversing the first magnetic field sensor, receiving, from a second magnetic sensor in a calibration device, second location signals responsive to the magnetic field emanating from the magnetic field generator and traversing the second magnetic field sensor, receiving, from a proximity sensor in the calibration device, a proximity signal indicating a contact with the calibration device, extracting, by a processor, respective location and orientation coordinates of the magnetic field sensors based on the signals, computing a conversion relation between the coordinates of the first magnetic field sensor and a distal end of the tool that is brought into contact with the calibration device, and subsequently applying the conversion relation, together with the coordinates of the first magnetic field sensor, in providing a visual indication of a location of the distal end of the tool inserted into a living body.

There is further provided, in accordance with an embodiment of the present invention, a computer software product, operated in conjunction with a rigid surgical tool having a first magnetic field attached to a proximal end of the rigid surgical tool, the product including a non-transitory computer-readable medium, in which program instructions are stored, which instructions, when read by a computer, cause the computer to receive, from the first magnetic field sensor, first location signals responsive to a magnetic field emanating from a magnetic field generator and traversing the first magnetic field sensor, to receive, from a second magnetic sensor in a calibration device, second location signals responsive to the magnetic field emanating from the magnetic field generator and traversing the second magnetic field sensor, to receive, from a proximity sensor in the calibration device, a proximity signal indicating a contact with the calibration device, to extract respective location and orientation coordinates of the magnetic field sensors based on the signals, to compute a conversion relation between the coordinates of the first magnetic field sensor and a distal end of the tool that is brought into contact with the calibration device, and to subsequently apply the conversion relation, together with the coordinates of the first magnetic field sensor, in providing a visual indication of a location of the distal end of the tool inserted into a living body.

BRIEF DESCRIPTION OF THE DRAWINGS

The disclosure is herein described, by way of example only, with reference to the accompanying drawings, wherein.

DETAILED DESCRIPTION OF EMBODIMENTS

During an otolaryngological procedure that uses a rigid surgical tool such as a rigid endoscope, it is important to track a distal end of the tool that may be hidden from direct view during the procedure. One way to perform such tracking is to incorporate a magnetic field sensor in the tool's distal end. However, there are many existing tools that do not have such distal end sensors, and where it is impractical to retrofit such a sensor.

Embodiments of the present invention provide systems and methods for calibrating a magnetic field sensor that can be removably attached to a rigid surgical tool. As described herein below, the system includes a magnetic field generator, a first magnetic field sensor, a calibration device, and a control unit, The first magnetic field sensor is configured for attachment to a proximal end of a rigid surgical tool configured to be inserted into a living body, and the calibration device includes a second magnetic field sensor and a proximity sensor, wherein the first and the second field sensors generate respective location signals responsive to a magnetic field emanating from the magnetic field generator and traversing the sensors. The proximity sensor generates a proximity signal indicating a contact with the calibration device.

In embodiments described herein, the control unit receives the signals from all the sensors, extracts respective location and orientation coordinates of the magnetic field sensors based on the signals, computes a conversion relation between the coordinates of the first magnetic field sensor and a distal end of the tool that is brought into contact with the calibration device, and subsequently applies the conversion relation, together with the coordinates of the first magnetic field sensor, in providing a visual indication of a location of the distal end of the tool inside the body.

System Description

Figure 1:
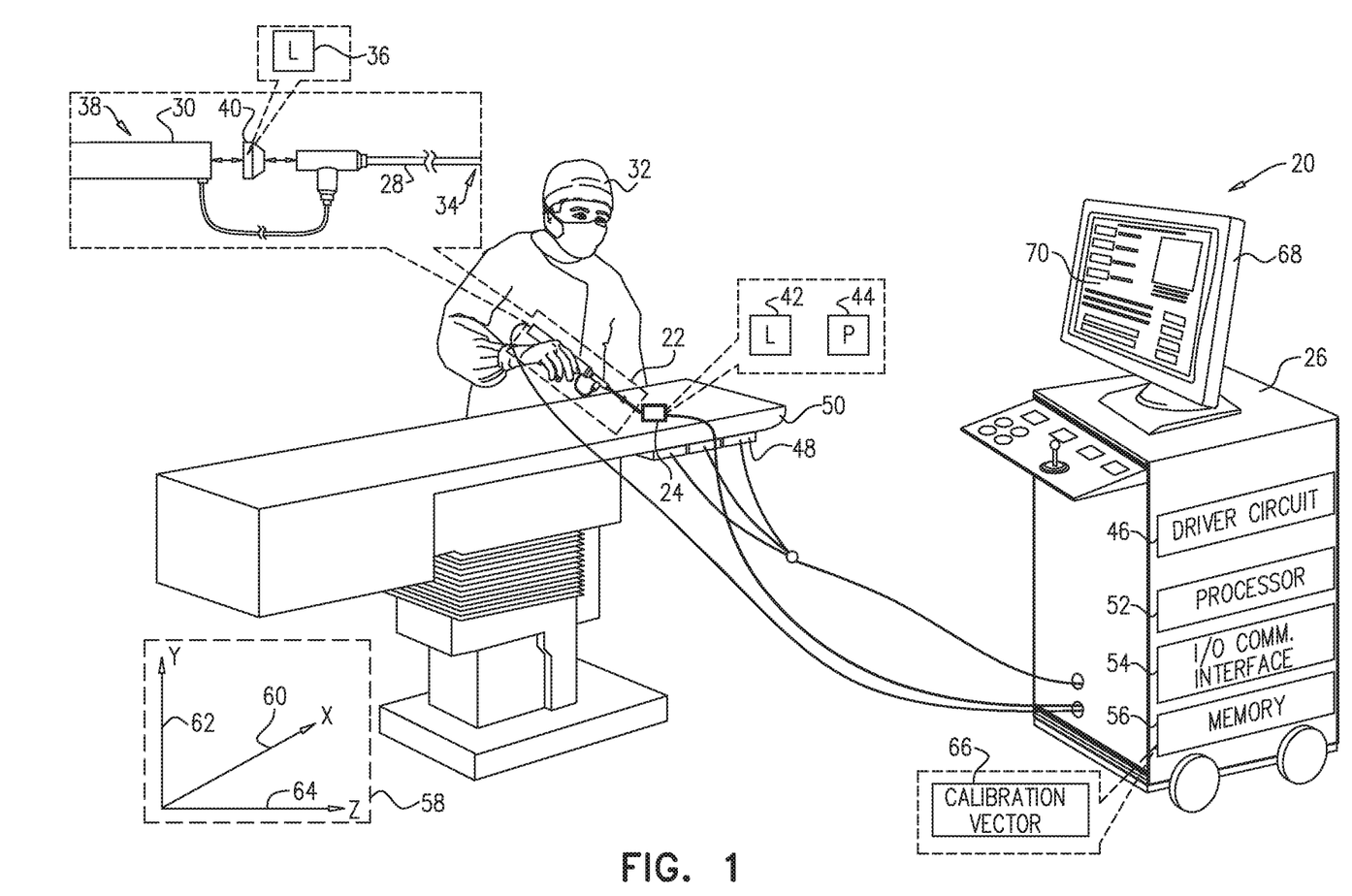
FIG. 1 is a schematic, pictorial illustration of a medical system comprising a rigid surgical tool having a removably attached magnetic field sensor, in accordance with an embodiment of the present invention.

FIG. 1 is a schematic, pictorial illustration of a medical system 20 comprising a rigid surgical tool 22, a calibration device 24 and a control console 26, in accordance with an embodiment of the present invention. In embodiments described herein, it is assumed that rigid surgical tool 22 is used for diagnostic or therapeutic treatment, such as minimally invasive catheter-based sinus surgery on a patient (not shown). Alternatively, rigid surgical tool 22 may be used, mutatis mutandis, for other therapeutic and/or diagnostic purposes.

Rigid surgical tool 22 comprises a rigid insertion tube 28 affixed to a handle 30 that a medical professional 32 can grasp and manipulate in order to insert a distal end 34 of the insertion tube into a lumen, such as a nasal cavity or a paranasal sinus, of a patient (not shown). Rigid surgical tool 22 also comprises a first magnetic field sensor 36 affixed to a proximal end 38 of the surgical tool. In some embodiments, first magnetic field sensor can be removably attached to proximal end 38. In the configuration shown in FIG. 1, first magnetic field sensor 36 is contained within a removable fixture 40 that couples to handle 30 and insertion tube 28.

Calibration device 24 comprises a second magnetic field sensor 42, and a proximity sensor 44. In some embodiments, proximity sensor 44 comprises a contact indicator that generates proximity signals that can provide an indication when the proximity sensor is touched. For example, proximity sensor 44 may comprise a force sensor that indicates the contact by a change of force, an optical sensor that indicates the contact by a change of light intensity, or an electrical sensor that indicates the contact by a change of an electrical parameter, such as current.

In embodiments described herein, medical system 20 uses magnetic position sensing to determine position coordinates of distal end 34 of surgical tool 22. To implement magnetic based position sensing, control console 26 comprises a driver circuit 46 which drives field generators 48 (also referred to herein collectively as the magnetic field generator) to generate magnetic fields within a three-dimensional (3D) volume above a table 50, the 3D volume including calibration device 24. Typically, field generators 48 comprise coils, which are placed below calibration device 24 at known positions external to the calibration device.

In addition to driver circuit 46, control console 26 comprises a processor 52, an input/output (I/O) communications interface 54, and a memory 56. Memory 56 may comprise any suitable volatile and/or non-volatile memory, such as random access memory, a hard disk drive, or a solid-state disk. I/O communications interface 54 enables the control console to transfer signals from, and/or transfer signals to magnetic field sensors 36 and 42 and proximity sensor 44. Magnetic field sensors 36 and 42, proximity sensor 44, and processor 52 are all coupled to I/O communications interface 54 via wired and/or wireless connections.

In some embodiments, each of the magnetic field sensors comprises a set of three orthogonal sensor coils, and field generators 48 comprise three orthogonally oriented generator coils. The generator coils, transmit alternating magnetic fields into a region within the 3D volume, the alternating magnetic fields traverse and induce signals in the magnetic field sensors, and processor 52 can analyze these signals to derive the location and orientation of the magnetic field sensors (i.e., with respect to the coils in field generator 48) in a coordinate system 58 comprising an X-axis 60, a Y-axis 62 and a Z-axis 64. Magnetic position tracking techniques are described, for example, in U.S. Pat. Nos. 5,391,199, 6,690,963, 5,443,489, 6,788,967, 5,558,091, 6,172,499 and 6,177,792, whose disclosures are incorporated herein by reference.

In embodiments of the present invention, processor 52 calibrates rigid surgical tool 22 by computing a conversion relation between the coordinates of the first magnetic field sensor and distal end 34. In some embodiments, processor 52 can store the conversion relation to memory 56 as a calibration vector 66 corresponding to the displacement between the first magnetic field sensor and distal end 34. During the calibration, processor 52 drives a display 68 (e.g., a LED monitor) to present location information 70 for the magnetic field sensors and the conversion relation.

Processor 52 typically comprises a general-purpose computer, with suitable front end and interface circuits for receiving signals from rigid surgical tool 22, calibration device 24, and to control the other components of control console 26. Processor 52 may be programmed in software to carry out the functions that are described herein. The software may be downloaded to control console 26 in electronic form, over a network, for example, or it may be provided on non-transitory tangible media, such as optical, magnetic or electronic memory media. Alternatively, some or all of the functions of processor 52 may be carried out by dedicated or programmable digital hardware components.

Rigid Surgical Tool Calibration

Figure 2:
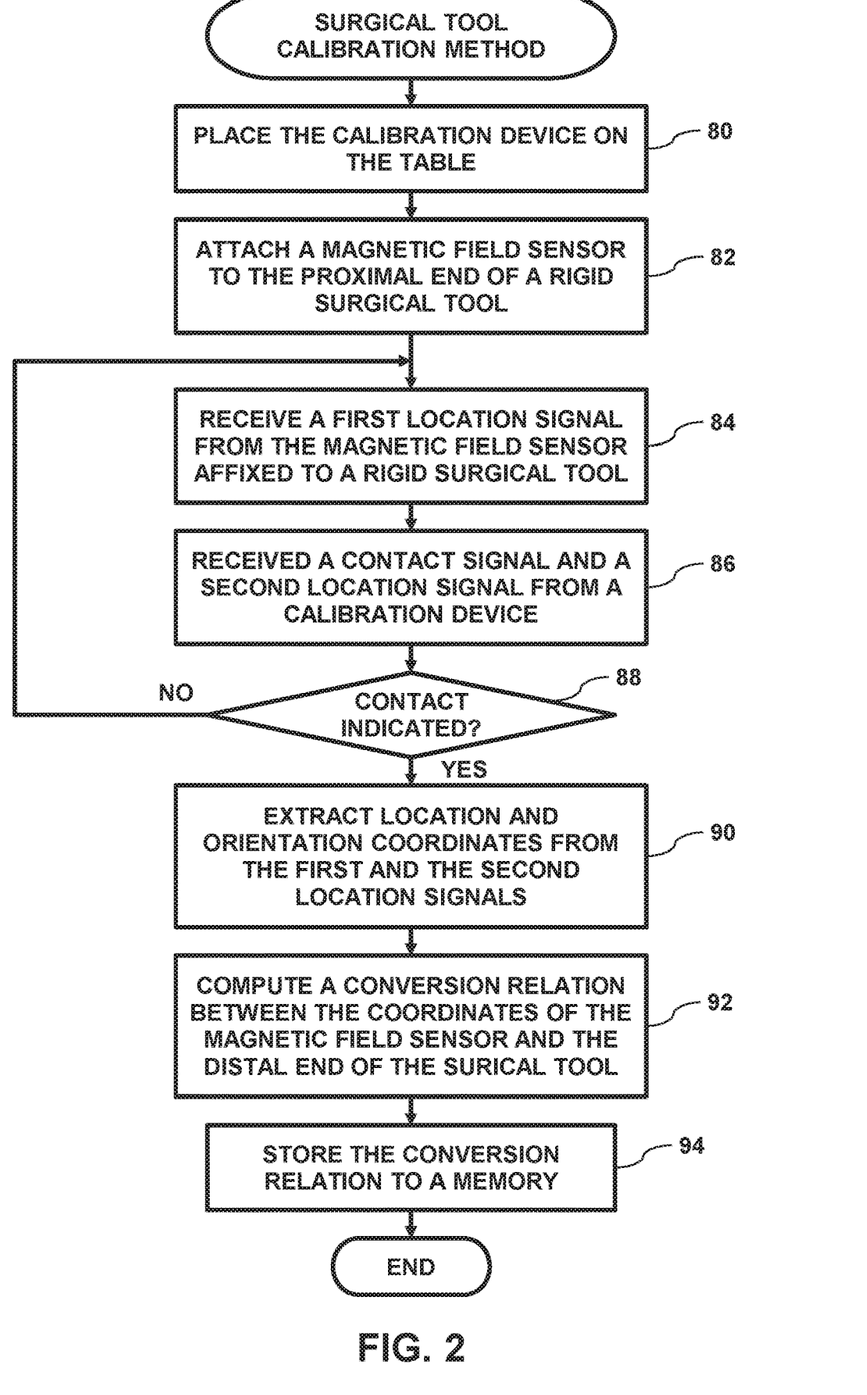
FIG. 2 is a flow diagram that schematically illustrates a method of computing a calibration vector for the rigid surgical tool, in accordance with an embodiment of the present invention.

FIG. 2 is a flow diagram that schematically illustrates a method for calibrating rigid surgical tool 22, in accordance with an embodiment of the present invention. In a placement step 80, medical professional 32 places calibration device 24 on table 50, and in an attach step 82, the medical professional attaches first magnetic field sensor 36 to proximal end 38 of rigid surgical tool 22. In the example shown in FIG. 1, medical professional 32 attaches the magnetic field sensor by fastening one end of removable fixture 40 to handle 30, and fastening the other end of the removable fixture to insertion tube 28.

Upon placing calibration device 24 on table 50 and attaching first magnetic field sensor 36 to proximal end 38, medical professional manipulates handle 30 so that distal end 34 of insertion tube 28 moves toward the calibration device. In a first receive step 84, processor 52 receives a first location signal from first magnetic field sensor 36, and in a second receive step 86, the processor receives a contact signal from proximity sensor 44, and a second location signal from second magnetic field sensor 42.

In a comparison step 88, if the contact signal does not indicate a contact (i.e., by distal end 34) with calibration device 24, then the method returns to step 84. However, if the contact signal indicates a contact with calibration device 24, then in in an extraction step 90, processor 52 extracts, from the location signals, location and orientation coordinates for magnetic field sensors 36 and 42. In a compute step 92, processor 52 computes, based on a specified length of insertion tube 28, a conversion relation between the location and orientation coordinates for magnetic field sensor 36 and distal end 34. In some embodiments, the conversion relation comprises an orientation and a distance between locations of first magnetic field sensor 36 and distal end 34 in coordinate system 58.

Finally, in a store step 94, processor 52 stores the conversion relation to memory 56, and the method ends. In some embodiments, processor can store, to memory 56, the conversion relation as calibration vector 66.

Figure 3:
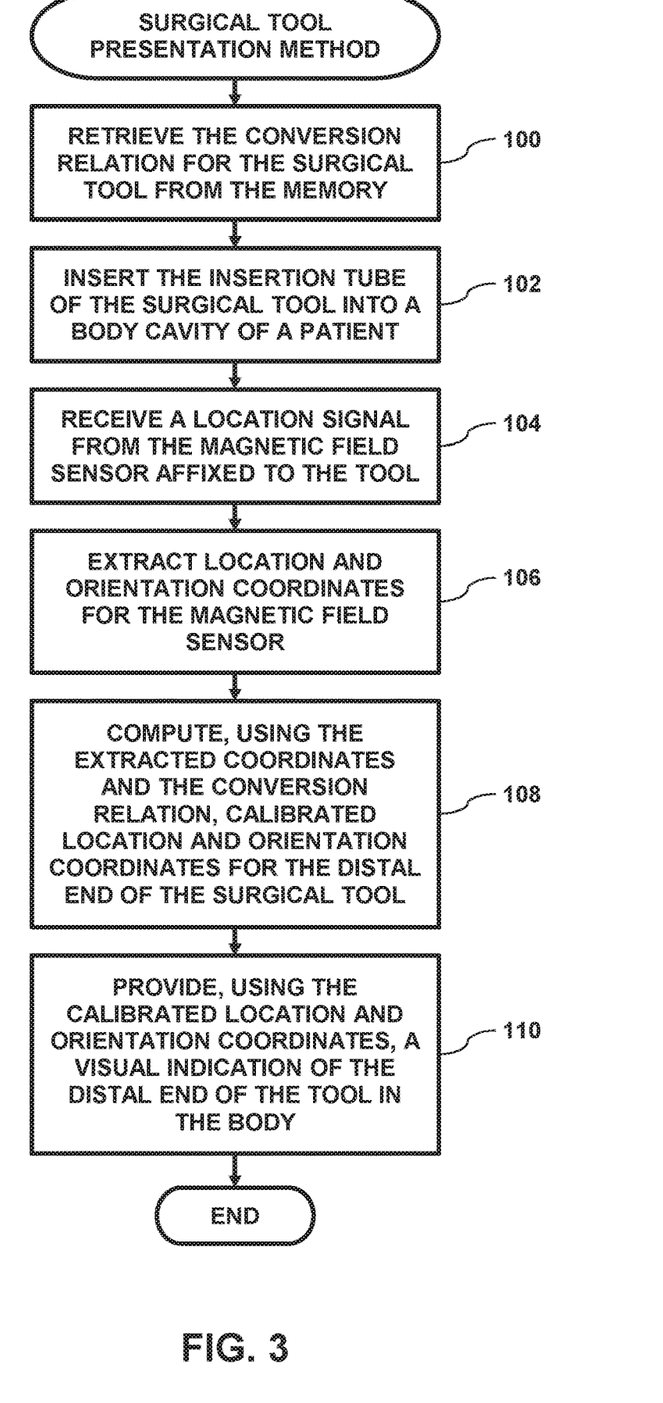
FIG. 3 is a flow diagram that schematically illustrates a method of using the calibration vector to determine a location of a distal end of the rigid surgical tool inserted into a body cavity of a patient, in accordance with an embodiment of the present invention.
Figure 4:
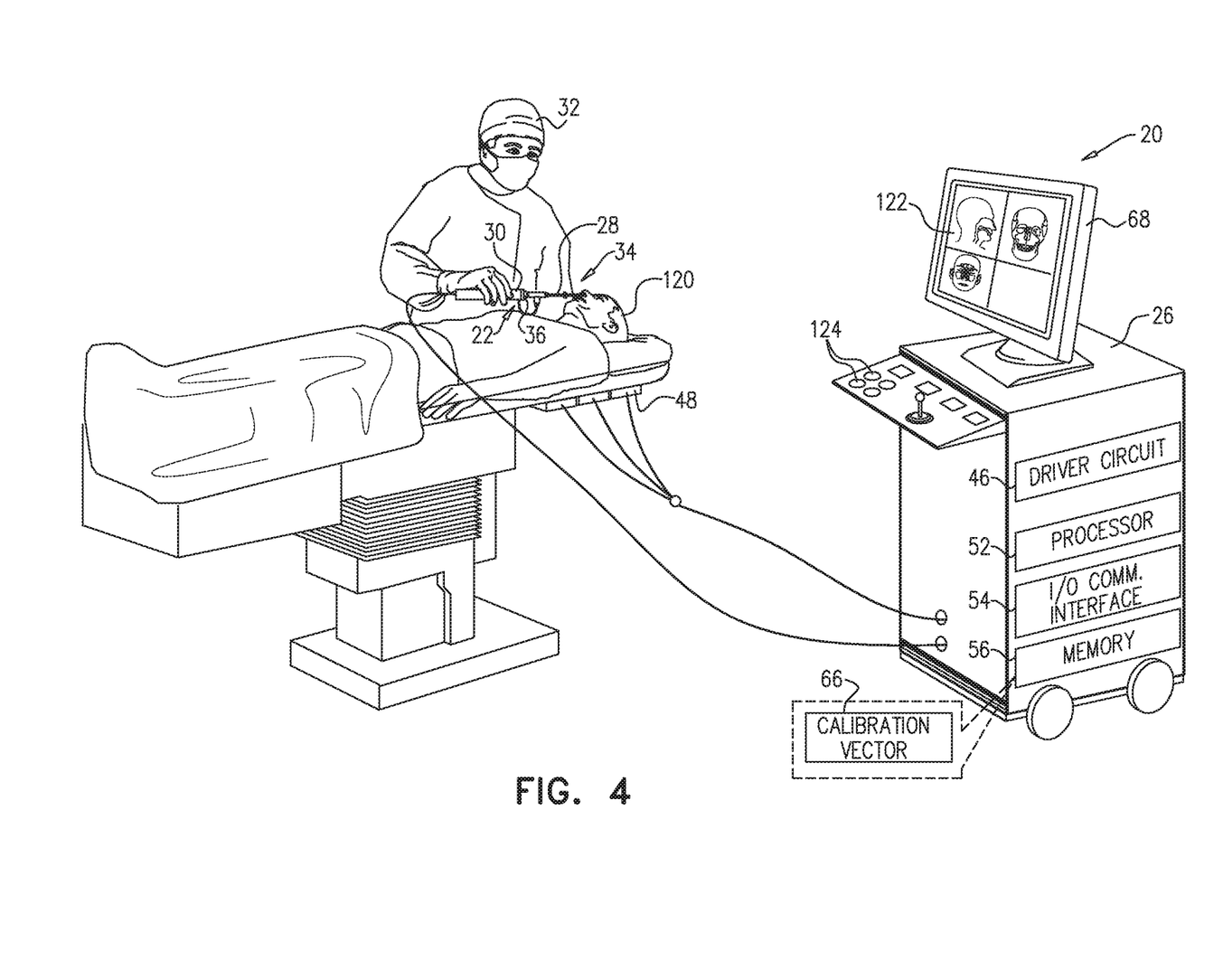
FIG. 4 is a schematic pictorial illustration of using the medical system to perform a procedure on the body cavity of the patient, in accordance with an embodiment of the present invention.
Figure 5:
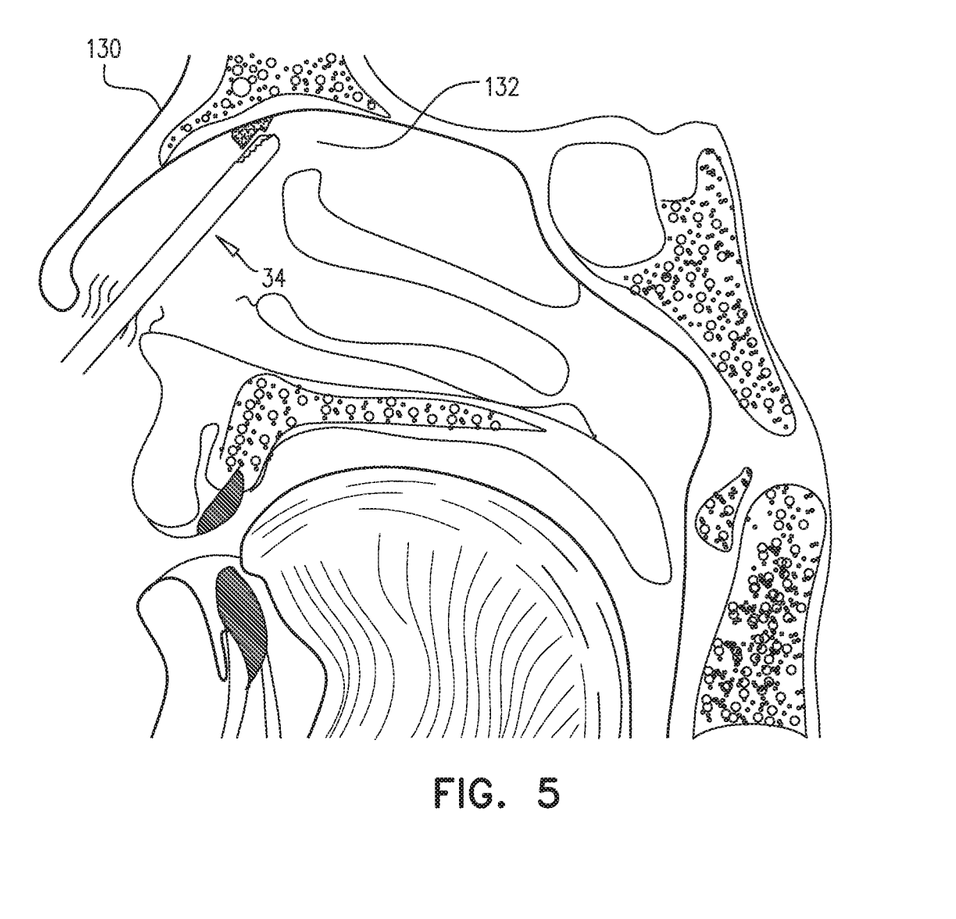
FIG. 5 is a schematic, pictorial illustration of the distal end of the rigid surgical tool inserted into the body cavity of the patient, in accordance with an embodiment of the present invention.

FIG. 3 is a flow diagram that schematically illustrates a method for presenting distal end 34 of rigid surgical tool on display 68, FIG. 4 is a schematic pictorial illustration of medical professional 32 using medical system 20 to perform a procedure on a patient 120 (also referred to herein as a living body), and FIG. 5 is a schematic pictorial illustration of distal end 34 of the rigid surgical tool inside a head 130 of the patient, in accordance with an embodiment of the present invention. In some embodiments, calibration device 24 can be placed on patient 120, typically before or during the procedure. It will be understood that calibration device 24 can be placed on any reference object, such as table 50 or patient 120, so long as signals from magnetic field sensor 42, generated in response to the fields from generators 48, enable processor 52 to measure the location and the orientation of the calibration device.

During the procedure, magnetic field generators 48 transmit alternating magnetic fields into a predefined working volume that contains a lumen such as a paranasal sinus within patient 120, the alternating magnetic fields induce signals in first magnetic field sensor 36, and processor 52 analyzes these signals to derive the location and orientation of the first magnetic field sensor with respect to the magnetic field generator. Additionally, during the procedure, processor 52 can present, on display 68, procedure information such as an image 122 that shows a current location of distal end 34 inside patient 120. In some embodiments, control console 26 may comprise one or more input devices 124 that medical professional can use during the procedure in order to manipulate the image.

In a retrieve step 100, processor 52 retrieves calibration vector 66 from memory 56, and in an insertion step 102, medical professional 32 inserts distal end insertion tube 28 into a body cavity of patient 120. In the example shown in FIG. 5, the body cavity comprises a sinus cavity 132 in head 130.

In a receive step 104, processor 52 receives a location signal from first magnetic field sensor 36, and in an extraction step 106, the processor extracts, from the received location signal using embodiments described supra, location and orientation coordinates in coordinate system 58 for the first magnetic field sensor. In a compute step 108, processor 52 uses the extracted location and orientation coordinates and the conversion relation of calibration vector 66 to compute location and orientation coordinates for distal end 34. Finally, in a visualization step 110, processor 52 uses the computed location and orientation coordinates to provide, in image 122, a visual indication of distal end 34 in patient 122, and the method ends.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An apparatus, comprising:
a magnetic field generator;
a first magnetic field sensor configured for attachment to a proximal end of a rigid surgical tool configured to be inserted into a living body, wherein the rigid surgical tool comprises a handle and an insertion tube, and wherein the first magnetic field sensor is configured to be coupled to the handle and the insertion tube and to be disposed coaxially with and between both the handle and the insertion tube when attached to the proximal end of the rigid surgical tool;
a calibration device, including a second magnetic field sensor and a proximity sensor, wherein the first and the second field sensors generate respective location signals responsive to a magnetic field emanating from the magnetic field generator and traversing the sensors, and wherein the proximity sensor generates a proximity signal indicating a contact with the calibration device; and
a control unit, which receives the signals from all the sensors, extracts respective location and orientation coordinates of the magnetic field sensors based on the signals, computes a conversion relation between the coordinates of the first magnetic field sensor and a distal end of the tool that is brought into contact with the calibration device, and subsequently applies the conversion relation, together with the coordinates of the first magnetic field sensor, in providing a visual indication of a location of the distal end of the tool inside the body.

2. The apparatus according to claim 1, wherein the rigid surgical tool comprises a rigid endoscope.

3. The apparatus according to claim 1, wherein the proximity sensor comprises a contact indicator.

4. The apparatus according to claim 3, wherein the proximity sensor is selected from a group consisting of a force sensor, an optical sensor and an electrical sensor.

5. The apparatus according to claim 1, wherein the first magnetic field sensor is configured to be removably attached to the proximal end of the rigid surgical tool.

6. The apparatus according to claim 1, and comprising a display configured to present the visual indication of the location of the distal end of the tool inside the body.

7. The apparatus according to claim 1, and comprising a memory, wherein the control unit is configured to store the computed conversion relation to the memory, and to retrieve the conversion relation from the memory.

8. The apparatus according to claim 1, wherein the conversion relation comprises an orientation and a distance between the location of the first magnetic field sensor and a location of the distal end.

9. The apparatus according to claim 1, wherein the magnetic field sensor is contained within a removable fixture having a proximal end connected to a distal end of the handle and a distal end connected to a proximal end of the insertion tube.

10. A method, comprising:
receiving, from a first magnetic field sensor attached to a proximal end of, and longitudinally interposed between a distal end of a handle and a proximal end of an insertion tube of, a rigid surgical tool, first location signals responsive to a magnetic field emanating from a magnetic field generator and traversing the first magnetic field sensor;
placing a calibration device comprising a second magnetic field sensor on a reference object in the magnetic field emanating from the magnetic field generator, wherein the magnetic field generator is disposed below the reference object;
receiving, from the second magnetic field sensor in the calibration device, second location signals responsive to the magnetic field emanating from the magnetic field generator and traversing the second magnetic field sensor;
receiving, from a proximity sensor in the calibration device, a proximity signal indicating a contact with the calibration device;
extracting, by a processor, respective location and orientation coordinates of the magnetic field sensors based on the signals;
computing a conversion relation between the coordinates of the first magnetic field sensor and a distal end of the tool that is brought into contact with the calibration device; and
subsequently applying the conversion relation, together with the coordinates of the first magnetic field sensor, in providing a visual indication of a location of the distal end of the tool inserted into a living body.

11. The method according to claim 10, wherein the rigid surgical tool comprises a rigid endoscope.

12. The method according to claim 10, wherein the proximity sensor comprises a contact indicator.

13. The method according to claim 12, wherein the proximity sensor is selected from a group consisting of a force sensor, an optical sensor and an electrical sensor.

14. The method according to claim 10, wherein the first magnetic field sensor is removably attached to the proximal end of the rigid surgical tool.

15. The method according to claim 10, wherein the reference object comprises a surface of the living body.

16. The method according to claim 10, wherein presenting the visual indication, comprises presenting, on a display, the location of the distal end of the tool inside the body.

17. The method according to claim 10, and comprising storing the computed conversion relation to a memory, and subsequently retrieving the conversion relation from the memory.

18. The method according to claim 10, wherein the conversion relation comprises an orientation and a distance between the location of the first magnetic field sensor and a location of the distal end.

19. The method according to claim 10, wherein the magnetic field generator is disposed below an operating table.

20. An apparatus, comprising:
a magnetic field generator;
a first magnetic field sensor attached a proximal end of a rigid surgical tool configured to be inserted into a living body, wherein the rigid surgical tool comprises a handle and an insertion tube;
a calibration device, including a second magnetic field sensor and a proximity sensor, wherein the first and the second field sensors generate respective location signals responsive to a magnetic field emanating from the magnetic field generator and traversing the sensors, and wherein the proximity sensor generates a proximity signal indicating a contact with the calibration device; and a control unit, which receives the signals from all the sensors, extracts respective location and orientation coordinates of the magnetic field sensors based on the signals, computes a conversion relation between the coordinates of the first magnetic field sensor and a distal end of the tool that is brought into contact with the calibration device, and subsequently applies the conversion relation, together with the coordinates of the first magnetic field sensor, in providing a visual indication of a location of the distal end of the tool inside the body;

wherein the insertion tube has a proximal end positioned at a distal end of the first magnetic field sensor and the handle has a distal end positioned at a proximal end of the first magnetic field sensor.

* * * * *